(12) United States Patent
Samarao et al.

(10) Patent No.: US 10,571,420 B2
(45) Date of Patent: Feb. 25, 2020

(54) NANOLAMINATE GAS SENSOR AND METHOD OF FABRICATING A NANOLAMINATE GAS SENSOR USING ATOMIC LAYER DEPOSITION

(71) Applicants: Gary O'Brien, Palo Alto, CA (US); Robert Bosch GmbH, Stuttgart (DE)

(72) Inventors: Ashwin K. Samarao, Sunnyvale, CA (US); Gary O'Brien, Palo Alto, CA (US)

(73) Assignee: Robert Bosch GmbH, Stuttgart (DE)

( * ) Notice: Subject to any disclaimer, the term of this patent is extended or adjusted under 35 U.S.C. 154(b) by 190 days.

(21) Appl. No.: 15/535,362

(22) PCT Filed: Dec. 14, 2015

(86) PCT No.: PCT/US2015/065555
§ 371 (c)(1),
(2) Date: Jun. 13, 2017

(87) PCT Pub. No.: WO2016/100210
PCT Pub. Date: Jun. 23, 2016

(65) Prior Publication Data
US 2017/0370865 A1 Dec. 28, 2017

Related U.S. Application Data

(60) Provisional application No. 62/097,500, filed on Dec. 29, 2014, provisional application No. 62/091,981, filed on Dec. 15, 2014.

(51) Int. Cl.
*G01N 27/12* (2006.01)
*G01N 21/77* (2006.01)
(Continued)

(52) U.S. Cl.
CPC ..... *G01N 27/125* (2013.01); *C23C 16/45525* (2013.01); *G01N 27/127* (2013.01); *G01N 33/004* (2013.01)

(58) Field of Classification Search
CPC .............................. G01N 27/12; G01N 21/77
(Continued)

(56) References Cited

U.S. PATENT DOCUMENTS 7,687,030 B2 * 3/2010 Uchiyama ............... G01N 21/77
422/88
2010/0166614 A1 * 7/2010 Uchiyama ............... G01N 27/12
422/98

(Continued)

FOREIGN PATENT DOCUMENTS

JP H04-273050 A 9/1992
JP 2002-131264 A 5/2002
(Continued)

OTHER PUBLICATIONS

International Search Report corresponding to PCT Application No. PCT/US2015/065555, dated Feb. 29, 2016 (3 pages).
(Continued)

*Primary Examiner* — Brian J. Sines
(74) *Attorney, Agent, or Firm* — Maginot, Moore & Beck LLP

(57) ABSTRACT

A thin film gas sensor device includes a substrate, a first electrode supported by the substrate, a second electrode supported by the substrate, and a gas-sensitive structure. The gas-sensitive structure is supported by the substrate and is electrically connected to the first and second electrodes. The gas sensitive structure includes a plurality of thin film layers of a first material vertically interleaved with a plurality of thin film layers of a second material. The first and second materials are mutually catalytic materials.

10 Claims, 7 Drawing Sheets

(51) Int. Cl.
*C23C 16/455* (2006.01)
*G01N 33/00* (2006.01)

(58) Field of Classification Search
USPC .............. 422/83, 82.01, 82.02; 436/43
See application file for complete search history.

(56) References Cited

U.S. PATENT DOCUMENTS

| 2012/0272721 A1 | 11/2012 | Kochupurackal et al. |
| 2014/0208830 A1 | 7/2014 | Buhler et al. |

FOREIGN PATENT DOCUMENTS

| JP | 3310444 B2 | 8/2002 |
| JP | 2002 286674 A | 10/2002 |
| JP | 2012-122814 A | 6/2012 |
| KR | 10-2011-0000917 A | 1/2011 |

OTHER PUBLICATIONS

Extended European Search Report corresponding to European Application No. 15870803.2, dated Jun. 18, 2018 (14 pages).

Diagne E H A et al, "Elaboration and characterization of tin oxide-lanthanum oxide mixed layers prepared by the electrostatic spray pyrolysis technique," Sensors and Actuators B: Chemical: International Journal Devoted to Research and Development of Physical and Chemical Transou, Elsevier BV, NL, vol. 78, No. 1-3, Aug. 30, 2001, pp. 98-105 (8 pages).

Fine et al, "Metal Oxide Semi-Conductor Gas Sensors in Environmental Monitoring," Sensors, vol. 10, No. 6, Jun. 1, 2010, pp. 5469-5502 (34 pages).

Kim D H et al, "Comparison of CO-gas sensing characteristics between mono- and multi-layer Pt/SnO"2 thin films," Sensors and Actuators B: Chemical: International Journal Devoted to Research and Development of Physical and Chemical Transdu, Elsevier BV, NL, vol. 77, No. 1-2, Jun. 15, 2001, pp. 427-431 (5 pages).

Rosental et al, "Epitaxial Single and Double Nanolayers of SnO2 and TiO2 for Resistive Gas Sensors," IEEE Sensors Journal, IEEE Service Center, New York, NY, US, vol. 13, No. 5, Jan. 9, 2013, pp. 1648-1655 (8 pages).

\* cited by examiner

NANOLAMINATE GAS SENSOR AND METHOD OF FABRICATING A NANOLAMINATE GAS SENSOR USING ATOMIC LAYER DEPOSITION

This application is a 35 U.S.C. § 371 National Stage Application of PCT/US2015/065555, filed on Dec. 14, 2015, which claims the benefit of priority of (i) U.S. provisional application Ser. No. 62/091,981, filed on Dec. 15, 2014, and (ii) U.S. provisional application Ser. No. 62/097,500, filed on Dec. 29, 2014. The disclosures of the above-identified patent applications are all incorporated by reference herein in their entirety.

FIELD

This disclosure relates generally to sensor devices and particularly to thin-film gas sensor devices.

BACKGROUND

Semiconductor gas sensors are used to detect the presence of a particular gas or gasses in an environment to which the sensor is exposed. A common type of gas sensor is a metal oxide semiconductor (MOS) gas sensor, which is also referred to as a "thick-film" gas sensor. FIG. 1 shows a prior art MOS gas sensor 10 including a substrate 14, a gas-sensitive portion 18 in electrical communication with electrodes 22, and a heating element 26. The gas-sensitive portion 18 is a thick-film that is configured to undergo a change in ionic conduction, electronic conduction, and/or optical transmittance in the presence of a target gas. The change of the gas-sensitive portion 18 is detected by an external read-out circuit (not shown) that is electrically connected to the electrodes 22. Typically, the change is exhibited as a change in the electrical resistance of the gas-sensitive portion 18, as measured by the read-out circuit. The heating element 26 is activated to heat the gas-sensitive portion 18 to a temperature that is suitable for detecting the target gas.

The ionic and/or electrical change in the gas-sensitive portion 18 in the presence of the target gas is a catalytic reaction. The surface of the gas sensitive portion 18 typically includes adsorbed molecules, which participate in the gas sensing process. For example, the surface of an n-type gas sensitive portion 18 typically includes adsorbed oxygen molecules. Each adsorbed oxygen molecule results in an electron hole (h*) that contributes to the electrical conduction of the gas sensitive portion 18 and tends to reduce the electrical resistance of the gas sensitive portion 18 according to the following formula:

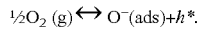
$$\tfrac{1}{2}O_2 (g) \leftrightarrow O^-(ads) + h^*.$$

When the n-type gas sensitive portion 18 is in contact with a molecule of the target gas, carbon monoxide (CO) for example, the gas sensitive portion undergoes a local change in chemical potential that leads to desorption of the adsorbed oxygen molecule according to the following formula:

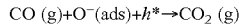
$$CO (g) + O^-(ads) + h^* \rightarrow CO_2 (g)$$

Along with desorption of the oxygen molecule, an electron is recombined with the hole (h*) to eliminate the hole, thereby increasing the electrical resistance of the gas sensitive portion, as sensed by the external read-out circuit. A corresponding relationship exists for a p-type gas sensitive portion 18, except that each adsorbed oxygen molecule gives rise to an electron instead of a hole (h*). Therefore, the underlying principle of operation of a MOS gas sensor includes exposing the gas sensitive portion 18 to a target gas, which results in a change in chemical potential of the gas sensitive portion. The change in chemical potential results in ionic/electronic exchange, which causes modulation of the electrical resistance of the gas sensitive portion 18. The modulation of the electrical resistance is sensed using the external read-out circuit and represents the presence, concentration, and/or the absence of the target gas.

The change in optical transmittance of a thick film gas sensor in the presence of the target gas is also a catalytic reaction. Optical thick film MOS gas sensors are found, for example, in carbon monoxide detectors and typically include an optical gas sensor and a corresponding read out circuit. The gas sensor includes a gas sensitive portion formed from a thick film of tin dioxide and nickel oxide, for example, that has been heat treated (annealed) at approximately 500° C. A heater circuit heats the thick film to an operating temperature, and the read out circuit monitors the optical transmittance of the heated thick film, which varies based on the concentration of carbon monoxide in the environment to which the detector is exposed In some instances it is desirable to "enhance" or "activate" the catalytic nature of the gas sensitive portion of a thick film MOS gas sensor. As an example, when either tin dioxide ($SnO_2$) or lanthanum oxide ($La_2O_3$) is used as the exclusive gas sensing material of a sensor device, the sensor device is unable to sense the presence of carbon dioxide ($CO_2$); however, when the two materials are layered upon each other, the junctions/boundaries of the materials are catalytically activated and become sensitive to carbon dioxide through a process referred to as mutual induction. Thus, tin dioxide and lanthanum oxide are referred to as being mutually catalytic materials.

As described above, MOS gas sensors are useful for sensing a target gas; however, fabricating a thick film MOS gas sensor can be difficult and time consuming, especially when the gas sensitive portion includes multiple layers of mutually catalytic materials. For example, to form the gas sensitive portion 18, powered tin dioxide and an organic binder are made into a paste that is screen printed onto the substrate 14. Then the substrate 14 and the paste are annealed at 600° C. for one hour. Next, lanthanum chloride ($LaCl_3$) and a solvent are applied to the annealed paste and are Joule heated (using the heating element 26, for example) to 120° C. for five minutes in order to evaporate the solvent. Thereafter, the Joule heated structure is annealed from 400° C. to 1200° C. in steps of 200° C. for five minutes to form the gas sensitive portion 18. The above described technique typically works well in a research environment, but is unsuitable for implementation in a mass-production line.

Therefore, for at least some of the above-described reasons, it is desirable to improve the structure and the process for fabricating semiconductor gas sensor devices.

SUMMARY

According to an exemplary embodiment of the disclosure, a thin film gas sensor device includes a substrate, a first electrode supported by the substrate, a second electrode supported by the substrate, and a gas-sensitive structure. The gas-sensitive structure is supported by the substrate and is electrically connected to the first and second electrodes. The gas sensitive structure includes a plurality of thin film layers of a first material vertically interleaved with a plurality of thin film layers of a second material. The first and second materials are mutually catalytic materials.

According to another exemplary embodiment of the disclosure, a method of forming a thin film gas sensor device includes forming a first electrode on a substrate, forming a second electrode on the substrate, and alternately depositing a continuous thin film layer of a first material and a continuous thin film layer of a second material on the substrate to form a multi-layered gas-sensitive structure, the multi-layered gas-sensitive structure electrically connected to the first and second electrodes. The first and second materials are mutually catalytic materials.

BRIEF DESCRIPTION OF THE FIGURES

The above-described features and advantages, as well as others, should become more readily apparent to those of ordinary skill in the art by reference to the following detailed description and the accompanying figures in which.

DETAILED DESCRIPTION

Figure 1:
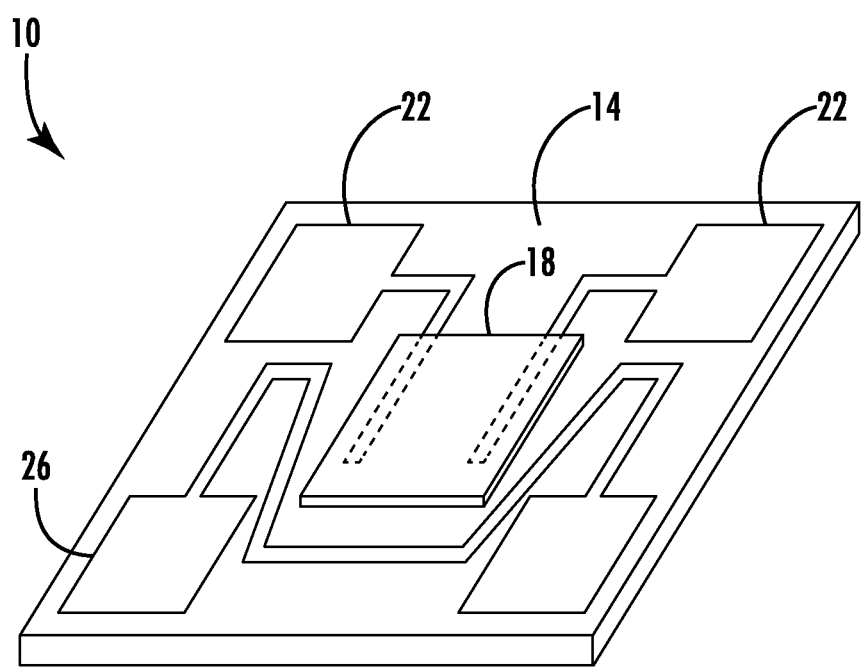
FIG. 1 is a perspective view of a prior art thick film MOS gas sensor device.

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

Figure 2:
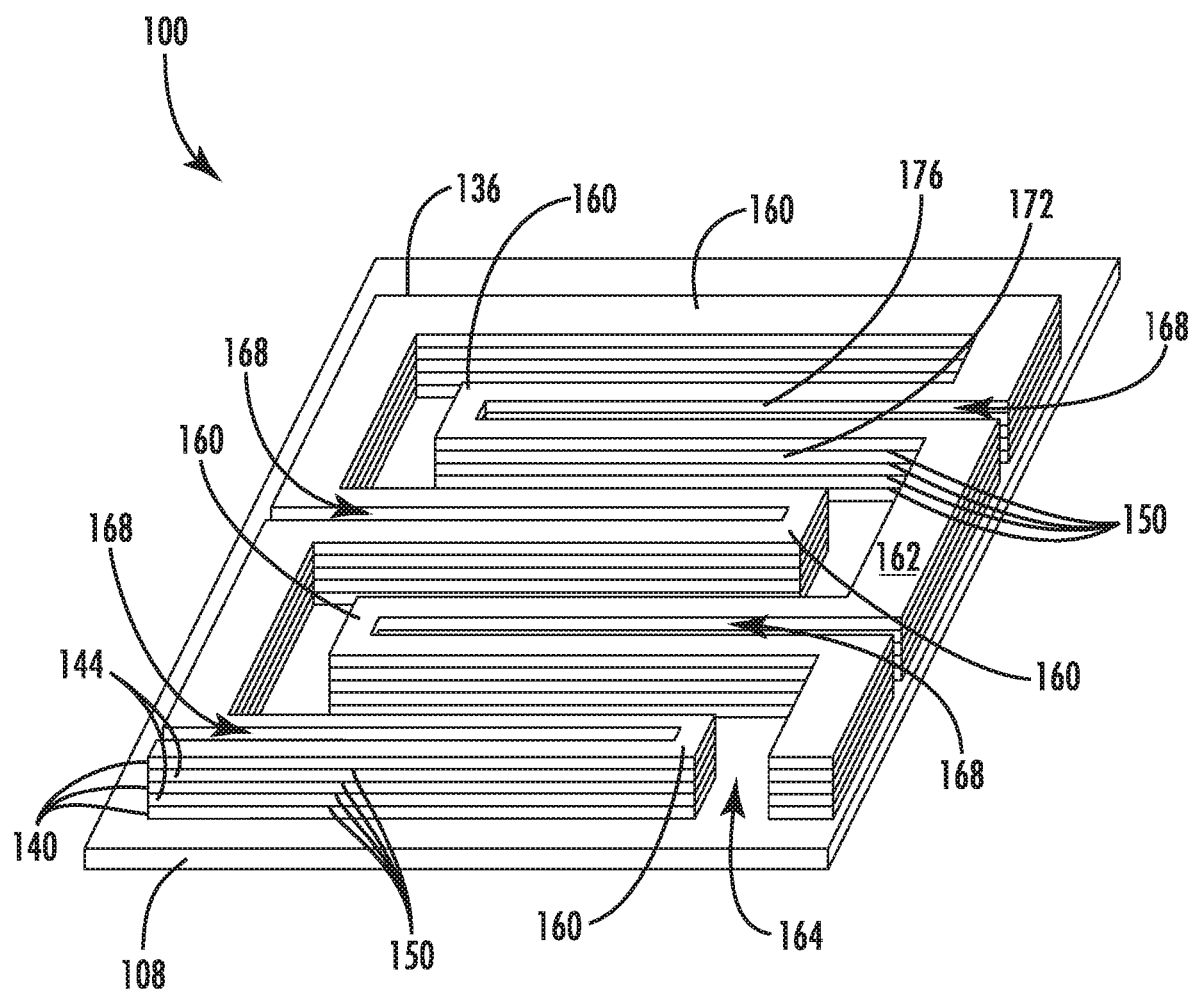
FIG. 2 is a perspective view of an exemplary nanolaminate thin film gas sensor device, as described herein, the sensor device includes an interdigitated laminated structure to increase the surface area of the sensor device that is configured to react with a target gas, in at least one embodiment, the sensor device is a resistance based sensor device that is associated with a non-optical electrical resistance based read out circuit.
Figure 3:
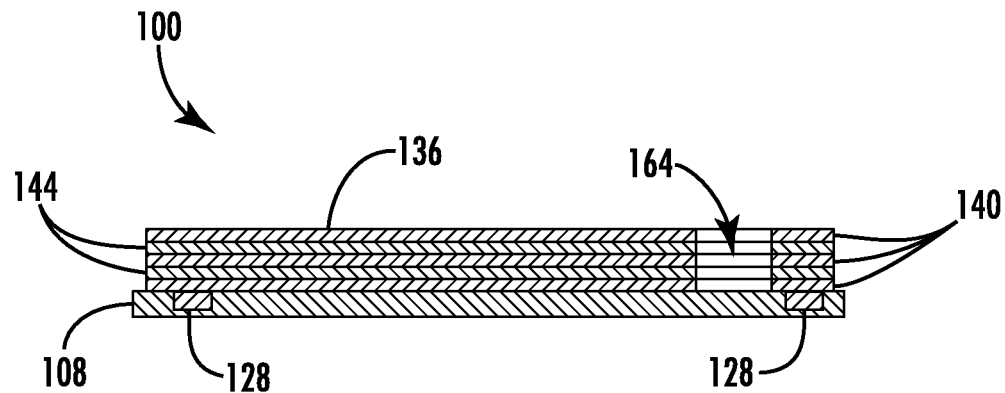
FIG. 3 is a cross sectional view of the sensor device of FIG. 2 taken along line III-III of FIG. 4 showing two electrodes of the sensor device.
Figure 4:
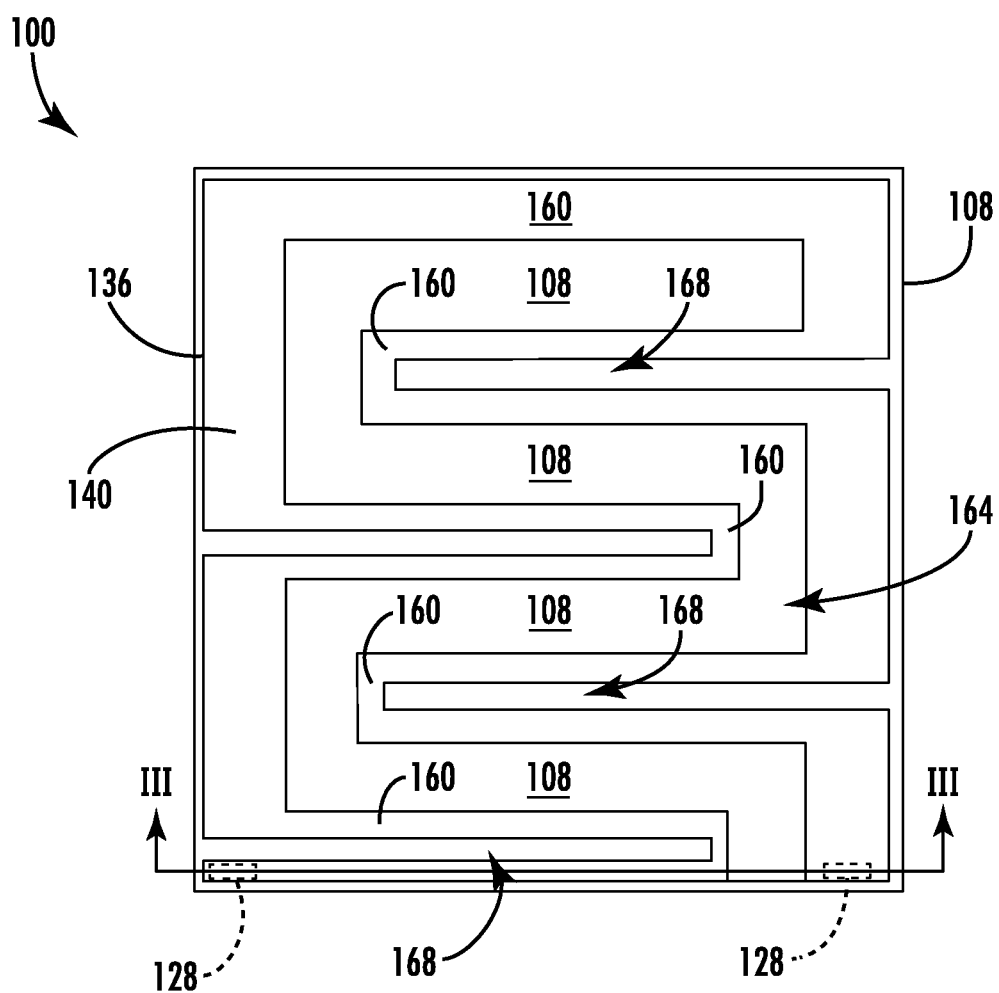
FIG. 4 is a top plan view of the sensor device of FIG. 2.

A semiconductor sensor assembly, which in this embodiment is a thin film gas sensor device 100, is shown in FIGS. 2-4. The exemplary embodiment of the sensor device 100 includes a substrate 108, at least two electrodes 128 (FIG. 3 and shown in phantom in FIG. 4), and at least one gas-sensitive structure 136.

The substrate 108 is formed from aluminum oxide or another desired type of electrically insulative substrate.

The electrodes 128 are supported by and/or located in the substrate 108 and are formed from an electrically conductive material, such as platinum or any other desired type of electrically conductive material. Electrical traces (not shown) may be electrically connected to the electrodes 128 in order to electrically connect the sensor device 100 to an external read-out circuit (not shown).

The gas-sensitive structure 136 is supported by the substrate 108 in electrical communication with the electrodes 128. In an exemplary embodiment, the structure 136 includes a plurality of vertically interleaved thin film layers 140, 144 of at least two mutually catalytic materials, which are configured to detect a target gas at exposed interfaces 150 (FIG. 2) thereof. When material A and material B are "mutually catalytic," the presence of material A causes material B to act as a catalyst and the presence of material B causes material A to act as a catalyst. "Thin film" layers are distinguished from "thick film" layers. As used herein, a thin film typically defines a thickness of less than 0.1 micrometers and is grown on a substrate as a series of stacked atomic thin layers using vacuum deposition processes, atomic layer deposition (ALD), and/or other such deposition processes. A thick film typically defines a thickness of greater than 100 micrometers and is formed by printing a paste on a substrate and then heating the substrate and paste to anneal the paste, thereby turning the paste into a glass-like structure. Thin films typically have controllable thickness at the angstrom level and an extremely uniform composition; whereas thick films typically have wide variations in thickness and composition. Thus, thin films have much more well-defined thicknesses and electrical characteristics as compared to thick films.

In an exemplary embodiment, the mutually catalytic materials include layer 140 of tin dioxide and layers 144 of lanthanum oxide, which together are configured to detect carbon dioxide (or other gasses). The exemplary embodiment of FIGS. 2-4 includes five layers of material including three tin dioxide layers 140 and two lanthanum oxide layers 144. Each junction of the layers 140, 144 is referred to herein as a mutually catalytic bi-layer or simply as a bi-layer. In other embodiments, the structure 136 includes any desired number of the layers 140, 144, such as from two to fifty layers. Furthermore, in other embodiments, the layers 140, 144 are formed from any desired material or materials that are configured to sense a desired target gas.

Although not shown in FIGS. 2 and 3, additional layers of other material may be included in the structure 136 that are not sensitive to the target gas and are not mutually catalytic with the layers 140, 144. For example, in some embodiments a layer or layers of a structural material may be included to increase the strength of the structure 136. Additionally, the structure 136 may include a porous layer or layers to enable the target gas to flow through a portion of the structure 136. Furthermore, the structure 136 may include a heater layer (not shown) that is configured to joule heat the layers 140, 144 to a predetermined operating temperature. Additional heat may be provided by the heater layer to "reset" the sensor device by clearing any adsorbed molecules from the structure 136. In embodiments of the sensor device 100 without a heater layer, at least one of the layers 140, 144 may function as a heater, because the layers 140, 144 are electrically conductive.

As shown in FIGS. 2 and 3, the layers 140, 144 each have approximately the same thickness. In some embodiments, however, the layers 140, 144 have different thickness. For example, in order to obtain a mutually catalytic effect from exemplary materials A and B it may be sufficient for the layers of material A to be five percent of the thickness of material B. In another embodiment, the mutually catalytic effect from exemplary materials A and B may be obtained when the layers of material A are five percent to eighty percent of the thickness of material B.

With reference to FIGS. 2 and 4, the structure 136 includes a plurality of digits 160 that are horizontally interleaved with each other to define an interdigitated arrangement. In the illustrated embodiment, the structure 136 defines five of the interleaved digits 160. Some of the digits 160 define a substantially "U" shape such that the electrical current flowing between the electrodes 128 is routed substantially completely through the digit. Other embodiments may define from two to fifty of the digits 160 based on at least the desired sensitivity of the structure 136 to the target gas, the concentration of the target gas, and the chemical structure of the target gas.

To define the digits 160, the structure 136 includes a serpentine shaped trench 164 and numerous digit trenches 168 that each extend completely through the structure 136. In other embodiments, the structure 136 is patterned with a trench or trenches of any desired shape, so long as the structure 136 is a unitary element through which electrical current is configured to flow between the electrodes 128. In another embodiment, the structure 136 is patterned with multiple trenches that are spaced apart from each other and configure the structure 136 as a unitary element.

Figure 5:
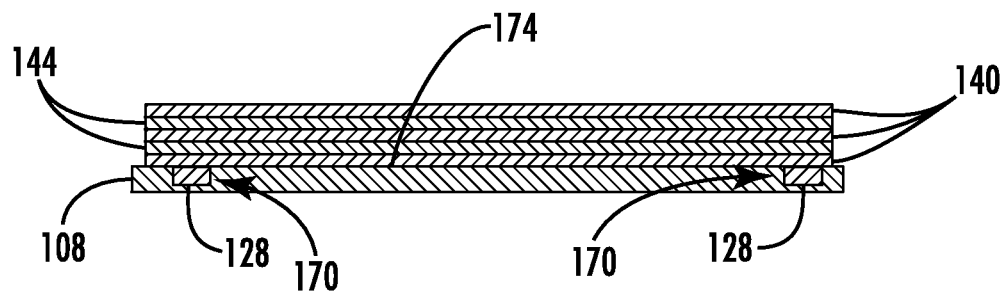
FIG. 5 is a cross sectional view taken along line V-V of FIG. 6, showing the laminated structure and the two electrodes supported on a substrate, the laminated structure is shown prior to being formed into the interdigitated configuration.
Figure 6:
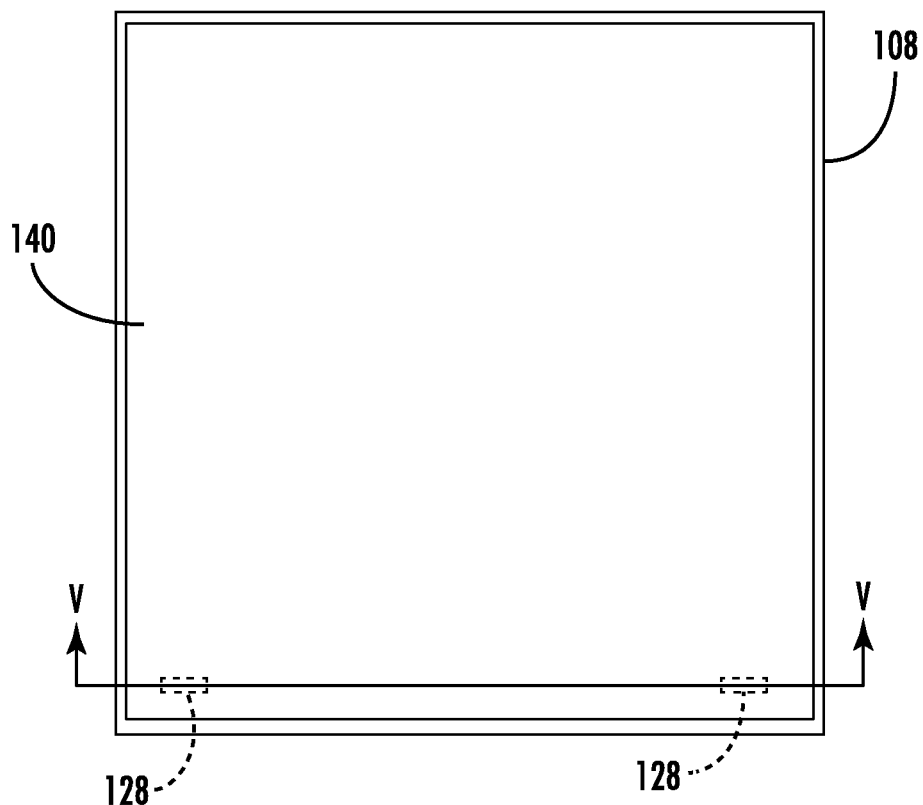
FIG. 6 is a top plan view of the structure of FIG. 5.

The interdigitated structure 136 is optimized for sensing the target gas. In particular, the digits 160 optimize the structure 136 by at least partially defining the area of the exposed interfaces 150 that is available for exposure to the target gas. Both an exterior surface 172 (FIG. 2) of the digits 160 and an interior surface 176 (FIG. 2) of the digits defining a digit trench 168 contributes to the area of the exposed interfaces 150. To illustrate, FIGS. 5 and 6 show the layers 140, 144 prior to the trenches 164, 168 being formed. In the "pre-trenched" configuration, the exposed interfaces 150 are present only at the periphery of the layers 140, 144, whereas the trenched structure 136 of FIGS. 2 and 4 includes exposed interfaces 150 at the periphery as well as at the exterior exposed sides of digits 160 and the interior exposed sides of the digits defining a digit trench 168. Thus, the interdigitated structure 136 has much more total area of exposed interfaces 150 than a corresponding "non-trenched" structure. The sensitivity of the sensor device 100 to the target gas is "tunable" based on at least the number of digits 160, the area of the trenches 164, 168, the area of the exposed interfaces 150, and the total number of the layers 140, 144.

With reference to FIG. 5, the sensor device 100 is fabricated/manufactured according to the following process. First, the substrate 108 is provided and patterned to define trenches 170 for receiving the material of the electrodes 128. Then, the material of the electrodes 128 is deposited into the trenches 170. Chemical mechanical planarization (CMP) may be used to remove some material of the electrodes 128 and the substrate 108, so that the electrodes are flush with an upper surface 174 of the substrate 108.

Next, the first layer 140 of the first material (e.g. tin dioxide) is formed on the substrate using atomic layer deposition (ALD) as a continuous layer. The first layer 140 is located in electrical communication with the electrodes 128.

ALD is used to deposit materials by exposing a substrate to several different precursors sequentially. A typical deposition cycle begins by exposing a substrate to a precursor "A" which reacts with the substrate surface until saturation. This is referred to as a "self-terminating reaction." Next, the substrate is exposed to a precursor "B" which reacts with the surface until saturation. The second self-terminating reaction reactivates the surface. Reactivation allows the precursor "A" to react with the surface. Typically, the precursors used in ALD include an organometallic precursor and an oxidizing agent such as water vapor or ozone.

The deposition cycle results, ideally, in one atomic sub-layer being formed on the substrate. Thereafter, another sub-layer may be formed by repeating the process. Accordingly, the final thickness of the layer is controlled by the number of cycles the substrate is exposed to. Moreover, deposition using an ALD process is substantially unaffected by the orientation of the particular surface upon which material is to be deposited. Accordingly, an extremely uniform thickness of material may be realized both on upper and lower horizontal surfaces and on vertical surfaces.

Next, the first layer 144 of the second material (e.g. lanthanum oxide) is formed on the first layer 140 using ALD as a continuous layer. Thereafter, alternating layers 140, 144 of the first and second materials are deposited as continuous layers until the desired total number of layers 140, 144 is formed.

After forming the continuous layers 140, 144, the layers are patterned to define the trenches 164, 168 and the exposed interfaces 150. In one embodiment, the continuous layers are patterned to define the trenches 164, 168 using ion milling. Ion milling is a process for removing material from a structure that includes firing ions at the structure in order to ablate certain portions of the structure. The ion milling process includes applying a photoresist layer to the upper-most continuous layer 140. The photoresist layer covers the structure 136 and substrate 108 except for the portions of the layers 140, 144 to be removed. Thus, the photoresist layer does not cover the area to be trenched. Then, the photoresist layer and the exposed portions of the layers 140, 144 are exposed to the ions to ablate selected portions of the layers, thereby defining the trenches 164, 168. In one embodiment, the ion milling process is controlled so as to avoid ablating the upper surface 174 of the substrate 108. The photoresist layer is removed from the structure 136 after the ion milling process In another embodiment, laser ablation is used to pattern the layers 140, 144 to define the trenches 164, 168 and the exposed interfaces 150. Laser ablation is a process that uses a laser device to selectively irradiate material from a sample using a laser beam typically by way of evaporation or sublimation. The laser device is controllable to irradiate the sample to a selected depth. Accordingly, laser ablation is usable to selectively irradiate the layers 140, 144 to define the trenches 164, 168 without irradiating the substrate 108.

In operation, the sensor device 100 is configured to sense the presence of a target gas or target gasses in a space in which the sensor device is positioned. Exemplary target gasses include carbon dioxide, carbon monoxide, nitrogen dioxide ($NO_2$), ammonia ($NH_3$), methane ($CH_4$), volatile organic compounds (VOCs), and the like. In an exemplary embodiment described herein, the tin dioxide layers 140 and the lanthanum oxide layers 144 are mutually inductive to sense carbon dioxide using an electrical resistance based read out circuit, thereby forming a non-optical carbon dioxide sensor, as described below. Due at least to the optimized area of the exposed interfaces 150 and the small size of the sensor device 100, the sensor device 100 is useful in most gas sensing applications including automobile exhaust systems, home appliances, laptops, handheld or portable computers, mobile telephones, smart phones, wireless devices, tablets, personal data assistants (PDAs), portable music players, film cameras, digital cameras, GPS receivers and other satellite navigation systems, electronic reading displays, projectors, cockpit controls, game consoles, earpieces, headsets, hearing aids, wearable display devices, security systems, and other applications as desired by those ordinary skill in the art.

Use of the sensor device 100 includes applying an electrical current to the electrodes 128 and the interdigitated structure 136 with an electrical energy source (not shown). In response to the electrical current, the structure 136 is quickly heated to a desired sensing temperature (i.e. a predetermined temperature) that is based on at least properties of the structure 136, the target gas, and the environment/space in which the sensor device 100 is positioned. Exemplary sensing temperatures range from one hundred fifty degrees Celsius to five hundred degrees Celsius; however, the sensor device 100 is configurable to operate at any desired sensing temperature.

The structure 136 is heated to the sensing temperature within a heating time period, which is referred to herein as a thermal time constant and a predetermined time period. The thermal time constant begins when electrical energy is applied to the structure 136 and ends when the structure 136 is heated to the sensing temperature.

Next, the heated sensor device 100 is exposed to a space in which at least one gas is present. A target gas may or may not be included in the at least one gas. If the target gas is present, then molecules of the target gas bind (adsorb) to the exposed interfaces 150, thereby changing an electrical/ionic property of the structure 136. The external read-out circuit senses the change in the electrical/ionic property, which represents the presence of the target gas. In one embodiment, a voltage drop across a resistor (not shown) connected in series with the structure 136 is detected/monitored by the external read-out circuit to determine the presence, absence, and/or concentration of the target gas. Accordingly, in one embodiment, the non-optical thin-film gas sensor device 100 is configured to detect carbon dioxide using a simple resistance based read out circuit. Therefore, the sensor device 100 and its associated read out circuit are more economical to manufacture as compared to optical-based carbon dioxide sensors and their associated read out circuits. The sensor device 100 is referred to as being "non-optical," because carbon dioxide is sensed based on a change in resistance instead of a change in an optical property. Typically, circuits configured to detect changes in resistance are less expensive and easier to maintain than circuited configured to detect changes in optical properties. In other embodiments, the sensor device 100 is operable to sense the target gas using any other desired transduction principle including, but not limited to, resistive, capacitive, and resonant frequency.

In addition to preparing the structure 136 for detecting and/or exposure to the target gas, the structure may be heated to "reset" the sensor device 100 through desorption. During desorption molecules are evacuated from the structure 136 in order to prepare the sensor device 100 for sensing additional quantities of the target gas or for sensing a different type/species of target gas.

Figure 7:
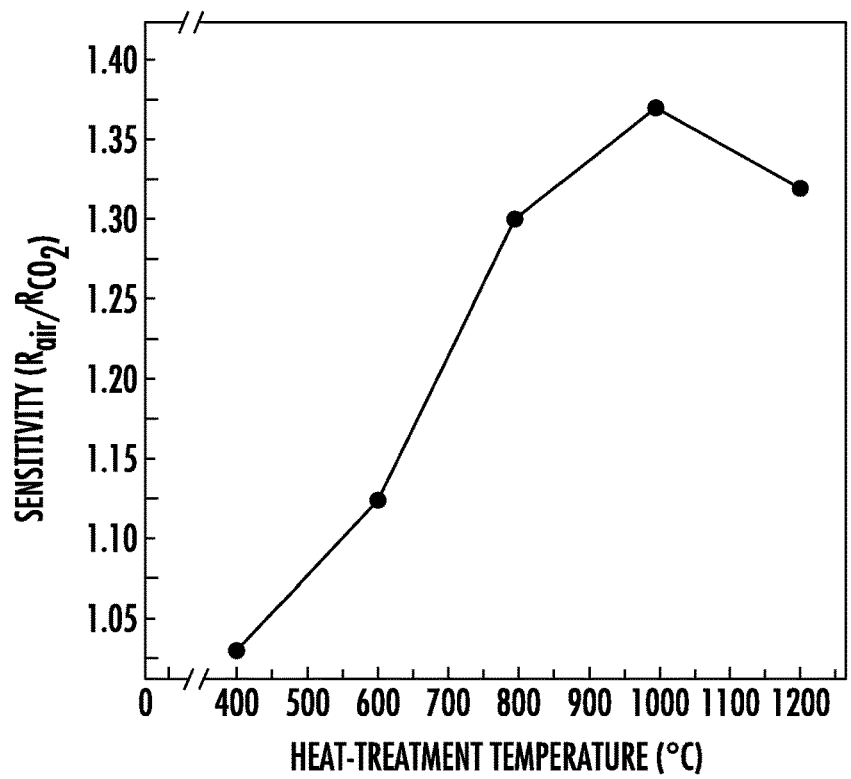
FIG. 7 is a graph of sensitivity to a target gas versus heat-treatment temperature for a thick film MOS gas sensor device having a gas sensitive portion formed from lanthanum oxide and tin dioxide.

The process described herein of using ALD to form the mutually catalytic thin film layers 140, 144 of tin dioxide and lanthanum oxide was informed by data collected in the process used to form the polycrystalline thick film gas sensitive portion 18 of the gas sensor 10 of FIG. 1. With reference to FIG. 7, the sensitivity of the sensor device 10, which includes a gas sensitive portion 18 having a thick film of polycrystalline lanthanum oxide and tin dioxide (for detecting carbon dioxide), is plotted versus the heat-treatment temperature (annealing temperature) of the gas sensor 10. The sensitivity of the sensor device 10 is a "unitless" quantity formed from the quotient of the measured resistance of the gas sensitive portion 18 in an atmosphere of air and the measured resistance of the gas sensitive portion 18 in an atmosphere of carbon dioxide.

Figure 8:
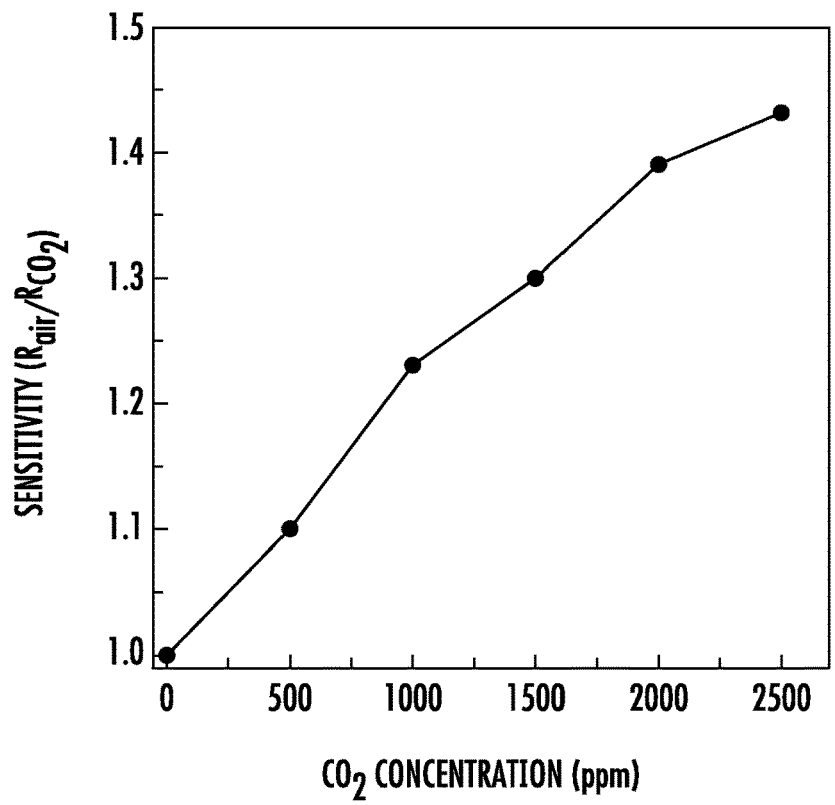
FIG. 8 is a graph of sensitivity to a target gas versus concentration of the target gas associated with a thick film MOS gas sensor device that has been heat treated to 1000° C.

As shown in the graph of FIG. 7, the sensitivity of the gas sensitive portion 18 to carbon dioxide increases for heat-treatment temperatures ranging from 400° C. to 1000° C. The graph also shows that the sensitivity of the gas sensitive portion 18 to carbon dioxide decreases for heat-treatment temperatures above 1000° C. Thus, the thick film gas sensitive portion 18 is optimized for sensing carbon dioxide when the gas sensitive portion is heat treated at approximately 1000° C. In forming the graph of FIG. 7, the sensor device 10 was placed in a measurement chamber maintained at 20° C. and the gas sensitive portion 18 was Joule heated to a sensing temperature of 400° C. The graph of FIG. 8 plots the sensitivity of a gas sensitive portion 18 that has been heat treated at 1000° C. for various concentrations of $CO_2$ to show the performance of the optimized thick film gas sensitive portion 18.

When polycrystalline thick film gas sensitive portion 18 is heat treated at 1000° C., the tin dioxide and the lanthanum oxide grow in a way that optimizes the surface area of the boundaries between the two materials without overgrowing each other. At heat treatment temperatures less than 1000° C., the formation of additional lanthanum oxide disrupts the balance of the surface area of the boundaries of the two materials, and at heat treatment temperatures greater than 1000° C. the formation of additional tin dioxide disrupts the balance of surface area of the boundaries of the two materials. At a heat treatment temperature of 1000° C., however, neither material overgrows the other, thereby resulting in an optimized surface area of the boundaries between the two materials. Thus, the graphs of FIGS. 7 and 8 and the insights developed therefrom support the finding that the carbon dioxide sensitivity of the polycrystalline thick film gas sensitive portion 18 occurs at the interfaces of the tin dioxide and lanthanum oxide through mutual induction.

Based on this insight, the sensor device 100 is fabricated using ALD in order to achieve the same balance of surface areas between the tin dioxide and lanthanum oxide, but with a less expensive, time consuming, and difficult process. ALD makes fabrication of the gas sensitive structure 136 faster, more economical, and easier (as compared to growing a thick film) by simplifying the process of forming a structure 136 with predetermined surface areas of exposed interfaces 150 that, in one embodiment, corresponds to the balance of surface areas of the gas sensitive portion 18 that is heat treated at 1000° C. The predetermined surface areas are achieved simply by controlling the number of layers 140, 144 and the size of the layers. Furthermore, heat treatment of the ALD deposited thin film layers 140, 144 is typically not required, thereby further simplifying the process.

Figure 9:
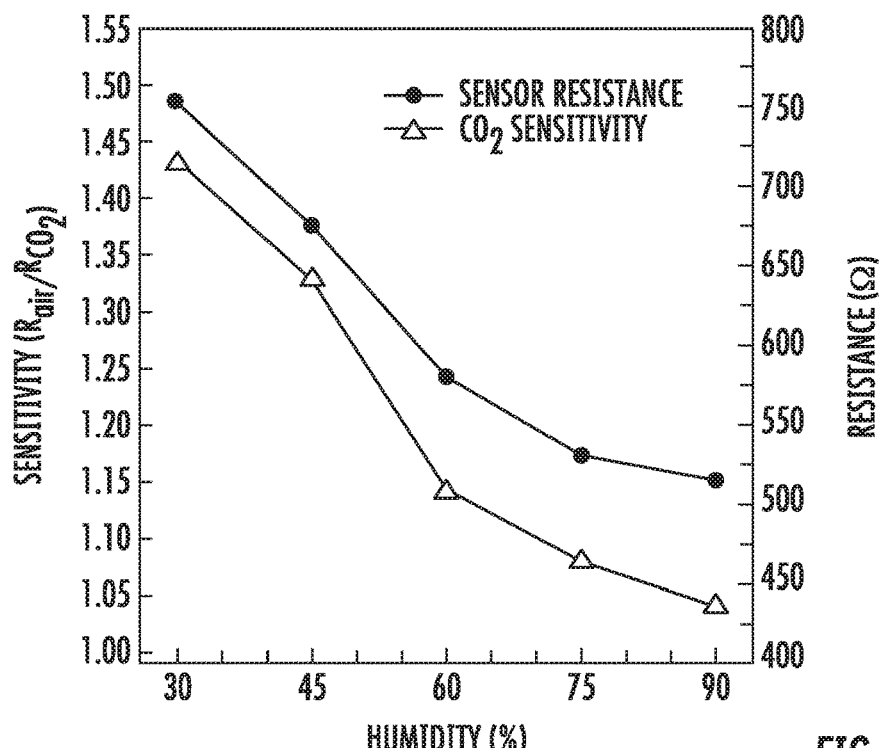
FIG. 9 is a graph of sensitivity to a target gas and resistance versus humidity associated with a thick film MOS gas sensor device having a gas sensitive portion formed from lanthanum oxide and tin dioxide.

As shown in FIG. 9, in addition to exhibiting a sensitivity to carbon dioxide, the layers 140, 144 are also sensitive to humidity (i.e. water vapor) in the environment. Specifically, the layers 144 of lanthanum oxide exhibit a sensitivity that is based on the humidity of the environment in which the sensor device 100 is located. The nanostructured lanthanum oxide layers 144 respond to humidity in much the same manner that bulk lanthanum oxide or thick films of lanthanum oxide respond to humidity, by exhibiting a reduction in electrical resistance that reduces the overall electrical resistance of the gas sensitive structure 136. Accordingly, a humidity sensor (not shown) having a sensor portion formed from lanthanum oxide only is usable to cancel out the effects of humidity on the sensor device 100.

Figure 10:
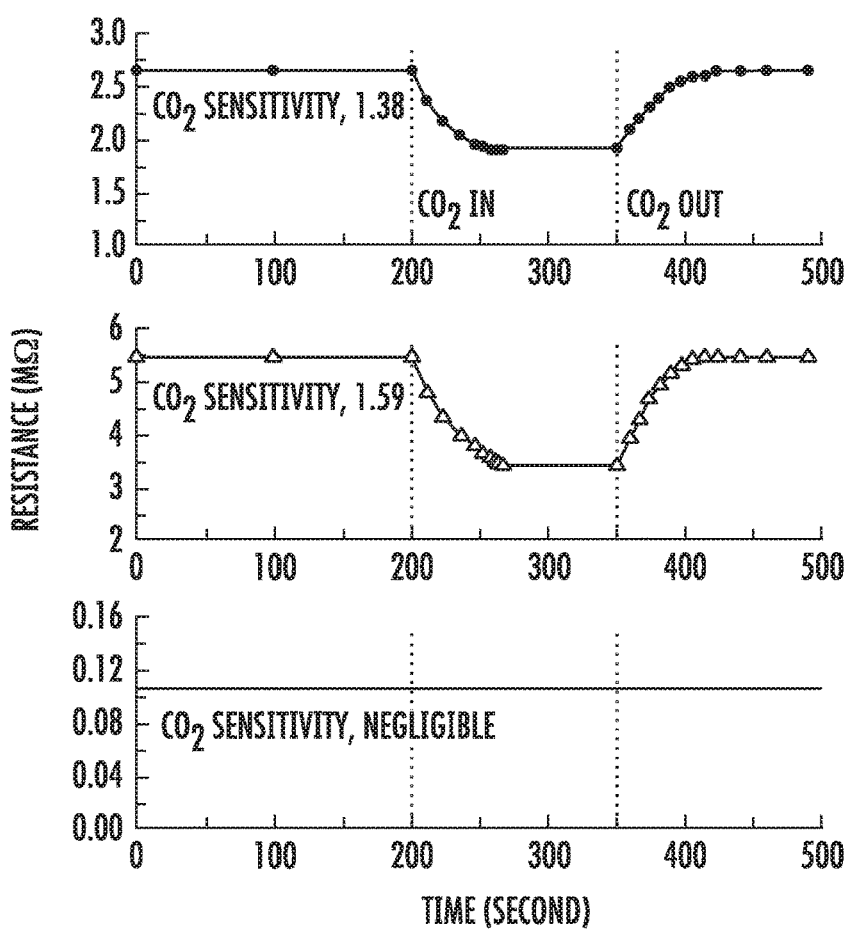
FIG. 10 is a graph of resistance versus time associated with a thick film MOS gas sensor device having a gas sensitive portion formed from lanthanum oxide and tin dioxide, in three different atmospheres including air, pure oxygen, and pure nitrogen.

As shown in FIG. 10, the environment in which the sensor device 100 is located may affect the sensitivity of the device 100. For example, the sensor device 100 including layers 140 of tin dioxide and layers 144 of lanthanum oxide is effective at sensing carbon dioxide in environments of air and environments of high oxygen content; however, the device 100 is less effective at sensing carbon dioxide in environments of high nitrogen content. The graphs (a), (b), and (c) of FIG. 10 illustrate this point. In graphs (a), (b), and (c), the electrical resistance of the tin dioxide layers 140 is plotted in an environment of air, an environment of oxygen ($O_2$), and an environment of nitrogen ($N_2$) respectively. In the graphs showing the response of the sensor device 100 in air (graph (a)) and oxygen (graph (b)) the sensor device 100 exhibits a change in resistance that is indicative of the presence of carbon dioxide; however, the response of the sensor device 100 to carbon dioxide in an environment of nitrogen (graph (c)) is negligible. In fact, as compared to the environment of air, the sensor device 100 is somewhat more sensitive to carbon dioxide in the environment of high oxygen content due to the oxygen increasing the adsorbed $O^-$. The environment of high nitrogen has an opposite effect that desorbs $O^-$ and makes the sensor device 100 substantially non responsive to carbon dioxide.

Figure 11:
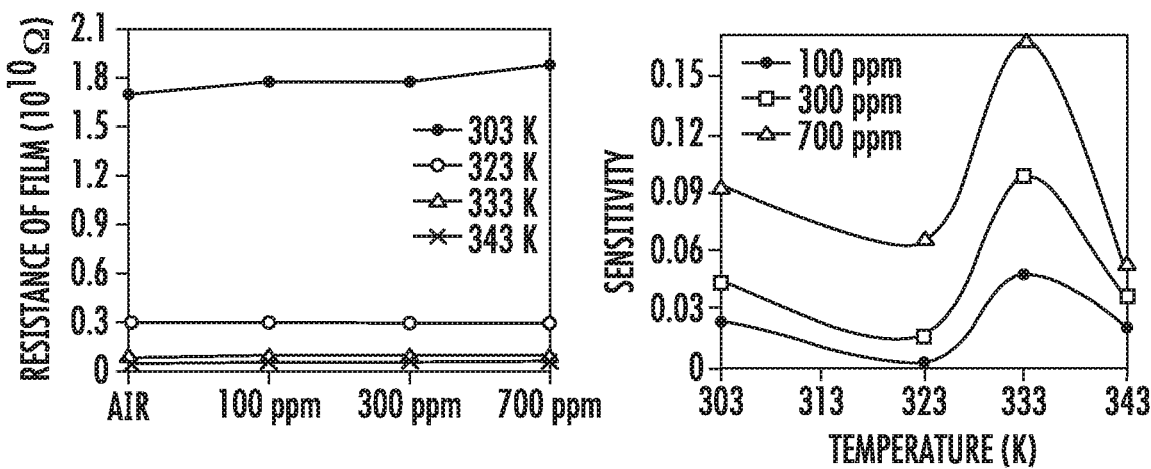
FIG. 11 includes a plot and a graph, the plot shows the resistance of a tin dioxide thin film at four different temperatures in each of air, an atmosphere of 100 ppm carbon dioxide, an atmosphere of 300 ppm carbon dioxide, and an atmosphere of 700 ppm carbon dioxide, the graph illustrates a sensitivity of the tin dioxide thin film to carbon dioxide versus temperature in each of three different atmospheres including an atmosphere of 100 ppm of carbon dioxide, an atmosphere of 300 ppm carbon dioxide, and an atmosphere of 700 ppm carbon dioxide.
Figure 12:
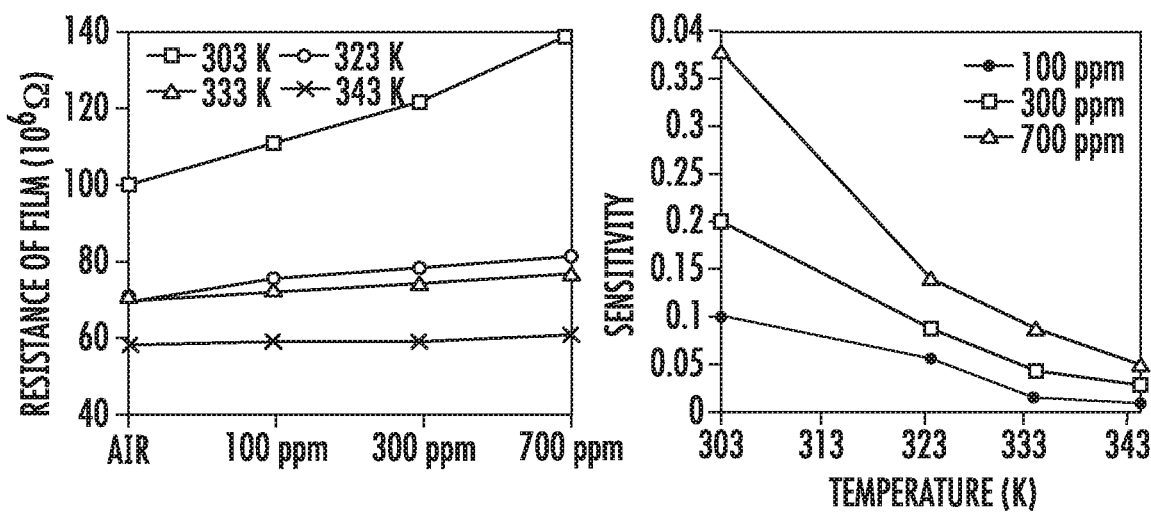
FIG. 12 illustrates a plot and a graph, the plot show the resistance of a layered thin film of tin dioxide on aluminum oxide at four different temperatures in each of air, an atmosphere of 100 ppm carbon dioxide, an atmosphere of 300 ppm carbon dioxide, and an atmosphere of 700 ppm carbon dioxide, the graph illustrates a sensitivity of the layered thin film to carbon dioxide versus temperature in each of three different atmospheres including an atmosphere of 100 ppm of carbon dioxide, an atmosphere of 300 ppm carbon dioxide, and an atmosphere of 700 ppm carbon dioxide.

In addition to a gas sensitive structure 136 formed from tin dioxide and lanthanum oxide, ALD enables nanolaminate structures of many other materials to be formed. For example, as shown in FIGS. 11 and 12, thick films of tin dioxide and aluminum oxide (instead of lanthanum oxide) are shown to exhibit sensitivity to carbon dioxide. In FIG. 11 the resistance and sensitivity of a thick film of only tin dioxide is shown to have a limited response to carbon dioxide, and in FIG. 12 the resistance and sensitivity of a thick film of tin dioxide and aluminum oxide is shown to have a greatly improved response. Specifically, in plot (a) of FIG. 11, the resistance of a thick film of tin dioxide is plotted in an environment of air, 100 ppm carbon dioxide, 300 ppm carbon dioxide, and 400 ppm carbon dioxide for operating temperatures of 303K, 323K, 333K, and 343K. In graph (b) of FIG. 11, the sensitivity of the thick film of tin dioxide for the above described environments is plotted versus temperature. Graph (b) of FIG. 11, shows that tin dioxide exhibits an optimized sensitivity to carbon dioxide when operated at approximately 333K in the above described environments.

The results of FIG. 11 are compared to FIG. 12, which show that for the same environments and temperatures a thick film of tin dioxide and aluminum oxide exhibits an optimized response to carbon dioxide when operated at 303K. Furthermore, the combination of tin dioxide and aluminum oxide has approximately twice the sensitivity of tin dioxide alone. This principle of operation is replicable with a nanostructured sensor device 100 including interleaved layers 140, 144 of tin dioxide and aluminum oxide.

In some applications it is beneficial to sense the presence and/or concentration of more than one gas in an environment. In such an application two separate gas sensors are employed; however, a simpler, smaller, and less expensive solution is to structure a sensor device to have multiple gas sensitive portions that are each sensitive to a different target gas. Accordingly, a plurality of the sensor devices 100 may be included on a single chip to form a gas sensor palette that is sensitive to a selected plurality of gasses. For example, a first sensor device 100 is fabricated with ALD to define a nanostructured gas sensitive portion that is sensitive to carbon dioxide. A second sensor device 100 is fabricated with ALD to define a nanostructured gas sensitive portion that is sensitive to carbon monoxide. The first and second sensor devices 100 may be included on the same chip to form a gas sensor palette that is sensitive to both carbon dioxide and carbon monoxide. This concept may be expanded to define a gas sensor palette that is sensitive to any number of gasses.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A thin film gas sensor device comprising:
   a substrate;
   a first electrode supported by the substrate;
   a second electrode supported by the substrate; and
   a gas-sensitive structure supported by the substrate and electrically connected to the first and second electrodes, the gas sensitive structure including a plurality of thin film layers of a first material vertically interleaved with a plurality of thin film layers of a second material, the first and second materials being mutually catalytic materials.

2. The thin film gas sensor device of claim 1, wherein the plurality of thin film layers of the first material and the plurality of thin film layers of the second material are formed using atomic layer deposition.

3. The thin film gas sensor device of claim 1, wherein the gas-sensitive portion includes a plurality of horizontally interleaved digits that are horizontally interleaved with each other to define an interdigitated arrangement.

4. The thin film gas sensor device of claim 3, wherein at least some digits of the plurality of horizontally interleaved digits are U-shaped.

5. The thin film gas sensor device of claim 3, wherein:
a serpentine-shaped trench extends through the gas-sensitive portion and defines at least some digits of the plurality of horizontally interleaved digits;
the serpentine-shaped trench including a first straight portion, a junction portion extending from the first straight portion, and a second adjacent straight portion extending from the junction portion; and
the junction portion is bounded on a first side by the gas-sensitive portion and is bounded on an opposite second side by the gas-sensitive portion.

6. The thin film gas sensor device of claim 1, wherein:
each layer of the first plurality of thin film layers defines a first thickness,
each layer of the second plurality of thin film layers defines a second thickness, and
the first thickness is different from the second thickness.

7. The thin film gas sensor device of claim 1, wherein the first plurality of thin film layers is formed from tin dioxide and the second plurality of thin film layers is formed from lanthanum oxide, such that the gas-sensitive portion undergoes a change in electrical resistance as measured between the first and second electrodes when exposed to carbon dioxide.

8. The thin film gas sensor device of claim 1, wherein:
at least one layer of the first and second plurality of thin film layers is configured as a heater layer, and
the heater layer is configured to joule heat the gas-sensitive portion to a predetermined operating temperature.

9. The thin film gas sensor device of claim 1, further comprising:
a third electrode supported by the substrate;
a fourth electrode supported by the substrate; and
another gas-sensitive structure supported by the substrate and electrically connected to the third and fourth electrodes, the other gas sensitive structure including a plurality of thin film layers of a third material vertically interleaved with a plurality of thin film layers of a fourth material, the third and fourth materials being mutually catalytic materials, and at least one of the third and fourth materials different from the first and second materials,
wherein the gas sensitive structure is configured to sense a first gas,
wherein the other gas sensitive structure is configured to sense a second gas, and
wherein the first gas is different from the second gas.

10. The thin film gas sensor device of claim 9, wherein:
the first gas is carbon dioxide, and
the second gas is carbon monoxide.

* * * * *